(12) United States Patent
Lee et al.

(10) Patent No.: US 6,900,245 B2
(45) Date of Patent: May 31, 2005

(54) PHARMACEUTICAL COMPOSITION COMPRISING CRYSTALLINE SIBUTRAMINE METHANESULFONATE HEMIHYDRATE

(75) Inventors: Jae-Heon Lee, Yongin-si (KR); Gha-Seung Park, Yongin-si (KR); Jae-Cheol Lee, Suwon-si (KR); Han-Kyong Kim, Yongin-si (KR); Young-Kil Chang, Seoul (KR); Gwan-Sun Lee, Seoul (KR)

(73) Assignee: Hanmi Pharm. Co., Ltd. (KR)

( * ) Notice: Subject to any disclaimer, the term of this patent is extended or adjusted under 35 U.S.C. 154(b) by 31 days.

(21) Appl. No.: 10/678,325

(22) Filed: Oct. 3, 2003

(65) Prior Publication Data

US 2004/0068018 A1 Apr. 8, 2004

(30) Foreign Application Priority Data

Oct. 5, 2002 (KR) .................................. 10-2002-0060798
Aug. 4, 2003 (KR) .................................. 10-2003-0053752

(51) Int. Cl.[7] ........................................... A61K 31/205
(52) U.S. Cl. ...................... 514/554; 514/553; 514/646; 562/115; 562/114; 562/30; 564/394; 564/442
(58) Field of Search ................................ 514/554, 553, 514/646; 564/394, 442; 562/114, 115, 30

(56) References Cited

U.S. PATENT DOCUMENTS 5,459,164 A * 10/1995 Vargas ........................ 514/646
6,162,831 A * 12/2000 Kelly et al. ................... 514/646
6,174,925 B1 * 1/2001 Bailey et al. ................. 514/646
6,187,820 B1 * 2/2001 Kelly et al. ................... 514/646
6,232,347 B1 * 5/2001 Mendel et al. ............... 514/646
6,355,685 B1 * 3/2002 Cheetham et al. ........... 514/646
6,365,631 B1 * 4/2002 Cheetham et al. ........... 514/646
6,376,551 B1 * 4/2002 Mendel et al. ............... 514/646
6,376,552 B1 * 4/2002 Mendel et al. ............... 514/646
6,376,554 B1 * 4/2002 Cheetham et al. ........... 514/646

FOREIGN PATENT DOCUMENTS

GB 2184122 * 11/1982
GB 2098302 * 6/1987

* cited by examiner

*Primary Examiner*—Samuel Barts
(74) *Attorney, Agent, or Firm*—Anderson Kill & Olick, PC (57) ABSTRACT

The present invention relates to a pharmaceutical composition for treating or preventing obesity, comprising novel crystalline sibutramine methanesulfonate hemihydrate of formula (I). The crystalline sibutramine methanesulfonate hemihydrate according to the present invention has a much higher solubility in water, and enhanced stability under a high humidity/temperature condition, as compared with sibutramine hydrochloride monohydrate (I)

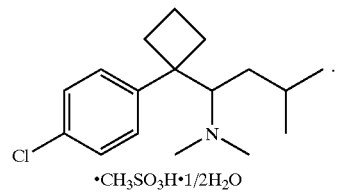

·$CH_3SO_3H·1/2H_2O$

29 Claims, 5 Drawing Sheets

PHARMACEUTICAL COMPOSITION COMPRISING CRYSTALLINE SIBUTRAMINE METHANESULFONATE HEMIHYDRATE

FIELD OF THE INVENTION

The present invention relates to a pharmaceutical composition for treating or preventing obesity, which comprises crystalline hemihydrate of sibutramine acid-addition salt.

BACKGROUND OF THE INVENTION

Sibutramine, N,N-dimethyl-1-[1-(4-chlorophenyl)-cyclobutyl]-3-methylbutylamine of formula (II);

(II)

may be used for preventing or treating depression, Parkinson's disease and obesity (see GB Patent No. 2,098,602, Korean Patent Publication Nos. 90-00274 and 99-164435, and International Publication No. WO 88/06444). Further, sibutramine may be used for reducing the resistance to insulin or enhancing the resistance to sugar, and for preventing or treating such diseases as gout, hyperuricemia, hyperlipemia, osteoarthritis, anxiety disorder, somnipathy, sexual dysfunction, chronic fatigue syndrome and cholelithiasis (see U.S. Pat. Nos. 6,174,925, 5,459,164, 6,187,820, 6,162,831, 6,232,347, 6,355,685, 6,365,631, 6,376,554, 6,376,551 and 6,376,552).

However, since sibutramine has a low melting point, it is used as an acid-addition salt in the pharmaceutical application.

GB Patent No. 2,098,302 and Korean Patent Publication No. 90-00274 disclose methods for preparing sibutramine and an anhydrous hydrochloride form thereof as a pharmaceutically acceptable acid-addition salt. However, anhydrous sibutramine hydrochloride is highly hygroscopic. Accordingly, it is difficult to use anhydrous sibutramine hydrochloride in a pharmaceutical composition.

In order to solve the above problem, non-hygroscopic sibutramine hydrochloride monohydrate of formula (IV) was developed (see GB Patent No. 2,184,122 and Korean Patent Publication No. 94-08913), e.g., for treating obesity.

·HCl·H₂O (IV)

However, sibutramine hydrochloride monohydrate of formula (IV) for treating obesity, e.g., Meridia and Reductil, has a relatively low solubility in water, for example 2.9 mg/ml at pH 5.2, which does not meet the lowest limit of the solubility desired of an active ingredient of a pharmaceutical composition (see Merck Index, 13th Ed, p1522).

Accordingly, there has been a need to develop a novel salt or hydrate of crystalline sibutramine, which is suitable for use in a pharmaceutical composition. The present inventors have therefore endeavored to develop sibutramine methanesulfonate hemihydrate, which has a high solubility in water and is non-hygroscopic, being stable under a high temperature/humidity condition.

SUMMARY OF THE INVENTION

It is therefore an object of the present invention to provide a pharmaceutical composition for treating or preventing obesity, comprising an acid-addition salt of sibutramine which has a high solubility in water and are stable under a high humidity/temperature condition.

It is another object of the present invention to provide a method for the preparation thereof.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

The present invention provides a pharmaceutical composition for treating or preventing obesity, comprising the novel crystalline sibutramine methanesulfonate hemihydrate of formula (I), which has a high solubility in water and high stability under a high humidity/temperature condition.

·CH₃SO₃H·1/2H₂O (I)

Further, the present invention provides crystalline sibutramine methanesulfonate hemihydrate of formula (I) and a method for the preparation thereof.

Herein, the term "sibutramine" refers to racemic sibutramine, unless otherwise indicated.

The crystalline sibutramine methanesulfonate hemihydrate of formula (I) has a high solubility in water, and is stable under a high humidity/temperature condition and non-hygroscopic, which is suitable for use in a pharmaceutical composition.

The 2θ values of major peaks observed in X-ray diffraction spectrum of the crystalline sibutramine methanesulfonate hemihydrate of formula (I) of the present invention are:

8.2±0.2, 10.8±0.2, 11.7±0.2, 12.0±0.2, 12.3±0.2, 15.8±0.2, 16.4±0.2, 17.4±0.2, 17.4±0.2, 17.8±0.2, 19.0±0.2, 21.2±0.2, 21.9±0.2, 22.2±0.2, 22.8±0.2, 23.3±0.2, 24.4±0.2, 24.9±0.2, 25.3±0.2, 25.6±0.2 and 26.8±0.2.

The present invention also provides two methods for preparing the crystalline sibutramine methanesulfonate hemihydrate of formula (I).

First, the crystalline sibutramine methanesulfonate hemihydrate of formula (I) may be prepared by reacting sibutramine of formula (II) with methanesulfonic acid in a mixture of an organic solvent and water (hereinafter, "the 1st method").

(II)

In the 1st method, methanesulfonic acid may be employed in an amount ranging from 1 to 2 mole equivalents, preferably from 1 to 1.2 mole equivalents, based on 1 mole of sibutramine of formula (II). Generally, methanesulfonic acid is dropwisely added to the substrate, which may be neat sibutramine or a solution thereof dissolved in an organic solvent.

The organic solvent may be an ester, an ether, a ketone, or a mixture thereof. The ester may be selected from the group consisting of ethyl acetate, n-propyl acetate, isopropyl acetate and n-butyl acetate; the ether, from the group consisting of diethyl ether, diisopropyl ether and t-butyl methyl ether; and the ketone, from the group consisting of acetone, methyl ethyl ketone and methyl isobutyl ketone. When a mixture of a ketone and ether is used, the ketone to ether ratio is preferably in ranging of 1:0.5 to 1:1.5, more preferably 1:2 to 1:3.

In this method, water may be employed in an amount ranging from 0.5 to 5 mole equivalents, based on 1 mole of sibutramine of formula (II), and the reaction is performed at a reaction temperature ranging from 0° C. to the boiling point of the solvent, preferably from 15 to 35° C., for 0.5 to 5 hrs after adding methanesulfonic acid.

Second, the crystalline sibutramine methanesulfonate hemihydrate of formula (I) may be prepared by (i) reacting sibutramine of formula (II) with methanesulfonic acid in an anhydrous organic solvent to obtain anhydrous sibutramine methanesulfonate of formula (III); and (ii) bringing the sibutramine methanesulfonate of formula (III) into contact with water in an organic solvent (hereinafter, "the 2nd method").

(II)

(III)

·CH₃SO₃H

In the 2nd method, methanesulfonic acid may be employed in an amount ranging from 1 to 2 mole equivalents, preferably from 1 to 1.2 mole equivalents, based on 1 mole of the sibutramine of formula (II). Generally, methanesulfonic acid is dropwisely added to neat sibutramine of formula (II) or a solution thereof dissolved in an organic solvent.

The organic solvent may be an ester, a ketone, an ether, toluene, or a mixture thereof. The ester may be selected from the group consisting of ethyl acetate, n-propyl acetate, isopropyl acetate and n-butyl acetate; the ketone, from the group consisting of acetone, methyl ethyl ketone and methyl isobutyl ketone; and the ether, from the group consisting of ethyl ether, isopropyl ether and t-butyl methyl ether.

When the organic solvent is a mixture of a ketone and ether, the ketone to ether ratio is preferably in the range of from 1:0.5 to 1:1.5, more preferably from 1:2 to 1:3.

In the 2nd method, water may be employed in an amount ranging from 0.5 to 5 mole equivalents, based on 1 mole of sibutramine of formula (II), and the reaction is performed at a temperature ranging from 0° C. to the boiling point of the solvent, preferably from 15 to 35° C., for 0.5 to 5 hrs after adding methanesulfonic acid. It is preferred that anhydrous sibutramine methanesulfonate of formula (III) is brought into contact with water for 2 hrs to 5 days.

Crystalline sibutramine methanesulfonate hemihydrate of formula (I) prepared according to the 1st or the 2nd method has a high solubility in water, and is non-hygroscopic and highly stable under a high humidity/temperature condition.

Examined for a comparative purpose was whether crystalline sibutramine methanesulfonate hemihydrate can be prepared from either of the enantiomers of sibutramine, (+)- and (−)-sibutramine. However, crystalline sibutramine methanesulfonate hemihydrate failed to form from (+)- and (−)-sibutramine.

Specifically, examined was whether crystalline sibutramine methanesulfonate hemihydrate can be prepared from (+)- and (−)-sibutramine separated from racemic sibutramine. Racemic sibutramine was optically resolved to obtain (+)- and (−)-sibutramine, according to the method disclosed in U.S. Patent Publication U.S. No. 2002/0006963, U.S. 2002/0006964 or International Patent publication No. WO 00/10551. Then, the (+)- and (−)-sibutramine were each treated according to the method of the present invention to see whether crystalline methanesulfonate hemihydrate can be prepared therefrom.

However, the (−)- or (+)-sibutramine failed to give crystalline methanesulfonate hemihydrate when the method according to the present invention is employed. Accordingly, the crystalline sibutramine methanesulfonate hemihydrate of the present invention is not easily conceivable by those skilled in the art.

The present invention includes a pharmaceutical composition for treating obesity and diseases related therewith, which comprises the crystalline sibutramine methanesulfonate hemihydrate of formula (I) as an active ingredient, and a pharmaceutically acceptable carrier, diluent, excipient or other additive.

Preferably, the pharmaceutical composition of the present invention is administrated as an oral formulation in the form of a tablet or capsule.

Tablets may be prepared by mixing the active ingredient with a carrier, diluent or excipient. Examples of the carrier, excipient and diluent employed in the pharmaceutical composition of the present invention are a disintegrator (e.g., starch, sugar and mannitol); a filler and extender (e.g., calcium phosphate and silicate derivatives); a binder (e.g., carboxymethyl cellulose and a derivative thereof, gelatin, and polyvinyl pyrrolidone); and a lubricant (e.g., talc, calcium stearate and magnesium stearate, and polyethylene glycol(s)).

Hard or soft capsules containing the active ingredient may be prepared without or with an additive such as a carrier, diluent and excipient, according to a conventional method.

Preferably, the effective amount of the crystalline sibutramine methanesulfonate hemihydrate of formula (I) in the inventive pharmaceutical composition ranges from 1 to 50 weight part, based on 250 weight part of the composition.

For example, the pharmaceutical composition may be prepared to contain 10 mg of crystalline sibutramine methanesulfonate hemihydrate of formula (I), 115 mg of fine crystalline cellulose, 115 mg of lactose, 5 mg of silicon dioxide and 5 mg of magnesium stearate. However, it should be understood that the amount of the active ingredient actually administered ought to be determined in light of various relevant factors including the condition of the patient to be treated, the age and weight, and the severity of the patient's symptom; and, therefore, the above composition ratio dose should not be intended to limit the scope of the invention in any way.

The following Examples are intended to further illustrate the present invention without limiting its scope.

PREPARATION EXAMPLE 1

Preparation of Sibutramine Hydrochloride Monohydrate of Formula (IV)

Anhydrous sibutramine hydrochloride was prepared according to the method disclosed in GB Patent No. 2,098, 602 or Korean Patent Publication No. 90-00274, and 10 g thereof was dissolved in a boiling mixture of acetone (110 ml) and water (1.2 ml), hot-filtered, and distillated to concentrate the filtrate, according to the method disclosed in GB Patent No. 2,184,122 or Korean Patent Publication No. 94-08913.

The concentrate was cooled and filtered to obtain crystals, and the crystals were dried under a vacuum to obtain 9.2 g of the title compound (Yield: 87%).

EXAMPLE 1

Preparation of Sibutramine Methanesulfonate Hemihydrate of Formula (I) by the $1^{st}$ Method 1-1) Procedure 1

30.0 g of sibutramine of formula (II) was dissolved in 120 ml of isopropyl acetate, 1.94 ml of water was added, and then 10.9 g of methanesulfonic acid was dropwisely added thereto. The reaction mixture was stilled for 1 hr, cooled to 0° C., again stirred for about 2 hrs, and then filtered to obtain crystals. The crystals were sequentially washed with 30 ml of isopropyl acetate and 30 ml of isopropyl ether, and then dried at 50° C. to obtain 38.46 g of the title compound as a white solid (Yield: 92.5%).

Melting point: 164~165° C. (shrunk at about 130° C.); Water content: 2.35% (Theoretical value: 2.34%); and $^1$H-NMR (δ, DMSO-d6): 8.5(1H, br. s), 7.7~7.2(4H, dd), 3.7(1H, t), 2.8(3H, d), 2.5(2H, d), 2.4(3H, s), 2.3(2H, d), 2.1(3H, d), 1.9(1H, m), 1.7~1.6(2H, m), 1.3(2H, t), 1.0(6H, t).

1-2) Procedure 2

10.0 g of sibutramine of formula (II) was dissolved in a mixture of 40 ml of ethyl acetate and 40 ml of t-butyl methyl ether, 0.97 ml of water was added, and then 3.8 g of methanesulfonic acid was dropwisely added thereto. The reaction mixture was stirred for 1 hr, cooled to 0° C., again stirred for about 2 hrs, and then filtered to obtain crystals. The crystals were sequentially washed with a mixture of 30 ml of isopropyl acetate and 30 ml of isopropyl ether, and then dried at 50° C. to obtain 12.1 g of the title compound as a white solid (Yield: 88%). The water content of the title compound was 2.38% (Theoretical value: 2.34%), and the melting point and the $^1$H-NMR data thereof were the same as those observed in 1-1).

1-3) Procedure 3

11.7 g of the title compound was prepared by repeating the procedure of the above 1-2) (Yield: 85%), except for employing 30 ml of acetone and 60 ml of t-butyl methyl ether, instead of 40 ml of ethyl acetate and 40 ml of t-butyl methyl ether. The water content of the title compound was 2.27% (Theoretical value: 2.34%), and the melting point and the $^1$H-NMR data thereof were the same as those observed in 1-1).

EXAMPLE 2

Preparation of Sibutramine Methanesulfonate Hemihydrate of Formula (I) by $2^{nd}$ Method 2-1) Preparation of Anhydrous Sibutramine Methanesulfonate of Formula (III) (Step 1 of the $2^{nd}$ Method)

2-1-1) Procedure 1

10.0 g of sibutramine of formula (II) was dissolved in 70 ml of acetone, and then 3.75 g of methanesulfonic acid was dropwisely added at room temperature. The reaction suspension was stirred for 1 hr, cooled to 0° C., again stirred for about 2 hrs, and then filtered to obtain crystals. The crystals were washed with 30 ml of ether, and then dried at 50° C. to obtain 11.7 g of the title compound as a white solid (Yield: 88%).

Melting point: 164~165° C.; Water content: 0.2%; and $^1$H-NMR (δ, DMSO-d6): 8.5(1H, br. s), 7.5(4H, dd), 3.7(1H, t), 2.8(3H, d), 2.5(2H, d), 2.4(3H, s), 2.3(2H, d), 2.1(3H, d), 1.9(1H, m), 1.7~1.6(2H, m), 1.42(2H, t), 1.0(6H, t).

2-1-2) Procedure 2

10.0 g of sibutramine of formula (II) was dissolved in 80 ml of toluene, and then 3.75 g of methanesulfonic acid was dropwisely added at room temperature. The reaction suspension was stirred for 2 hrs, cooled to 0° C., stirred for about 2 hrs, and then filtered to obtain crystals. The crystals were washed with 20 ml of ether and then dried at 50° C. to obtain 12.8 g of the title compound as a white solid (Yield: 95). The water content of the title compound was 0.1%, and the melting point and the $^1$H-NMR data thereof were the same as those observed in 2-1-1).

2-1-3) Procedure 3

12.5 g of the title compound as a white solid was prepared by repeating the procedure of the above 2-1-2) (Yield: 93%), except for using isopropyl acetate instead of toluene. The water content of the product was 2.27% (Theoretical value: 2.34%), and the melting point and the $^1$H-NMR data thereof were the same as those observed in 2-1-1).

2-2) Preparation of Sibutramine Methanesulfonate Hemihydrate of Formula (I) (step 2 of the $2^{nd}$ method)

2-2-1) Procedure 1

5.0 g of anhydrous sibutramine methanesulfonate of formula (III) prepared in any one of 2-1-1) to 2-1-3) was dissolved in a mixture of 50 ml of ether and 25 ml of acetone, and then 0.72 ml of water was added thereto. The reaction mixture was stirred for 18 hrs at room temperature, and then filtered to obtain crystals. The crystals were washed with 10 ml of a mixture of ether and acetone (2:1 v/v), dried at 50° C. to obtain 3.89 g of the title compound as a white solid (Yield: 76%). The water content of the obtained compound was 2.30% (Theoretical value: 2.34%), and the melting point and the $^1$H-NMR data thereof was the same as those observed in 1-1).

2-2-2) Procedure 2

10.0 g of anhydrous sibutramine methanesulfonate of formula (III) prepared in any one of 2-1-1) to 2-1-3) was dissolved in a mixture of 100 ml of ether and 40 ml of methyl isobutyl ketone, and then 1.44 ml of water was added thereto. The reaction mixture was stirred for 24 hrs at room temperature and then filtered to obtain crystals. The crystals were washed with 30 ml of a mixture of ether and methyl ethyl ketone (2:1 v/v), dried at 50° C. under warm wind to obtain 7.5 g of the title compound as a white solid (Yield: 73%). The water content of the obtained compound was 2.32% (Theoretical value: 2.34%), and the melting point and the $^1$H-NMR data thereof were the same as those observed in 1-1).

EXAMPLE 3

Qualitative Analysis of the Structure of Crystalline Sibutramine Methanesulfonate Hemihydrate of Formula (I)

Powder X-ray diffraction data and a differential scanning calorimeter thermogram showed that crystal shape of sibutramine methanesulfonate hemihydrate of formula (I) was different from either anhydrous sibutramine methanesulfonate of formula (II) or sibutramine hydrochloride monohydrate of formula (IV) (see FIGS. 1 to 5).

The powder X-ray diffraction spectrum of sibutramine methanesulfonate hemihydrate of formula (I) showed characteristic peaks (FIG. 1), which are represented in Table 1. In table 1, "2θ", "d" and "$I/I_o$" mean the diffraction angel, the distance between crystal facets, and the relative peak intensity, respectively.

TABLE 1

Figure 1:
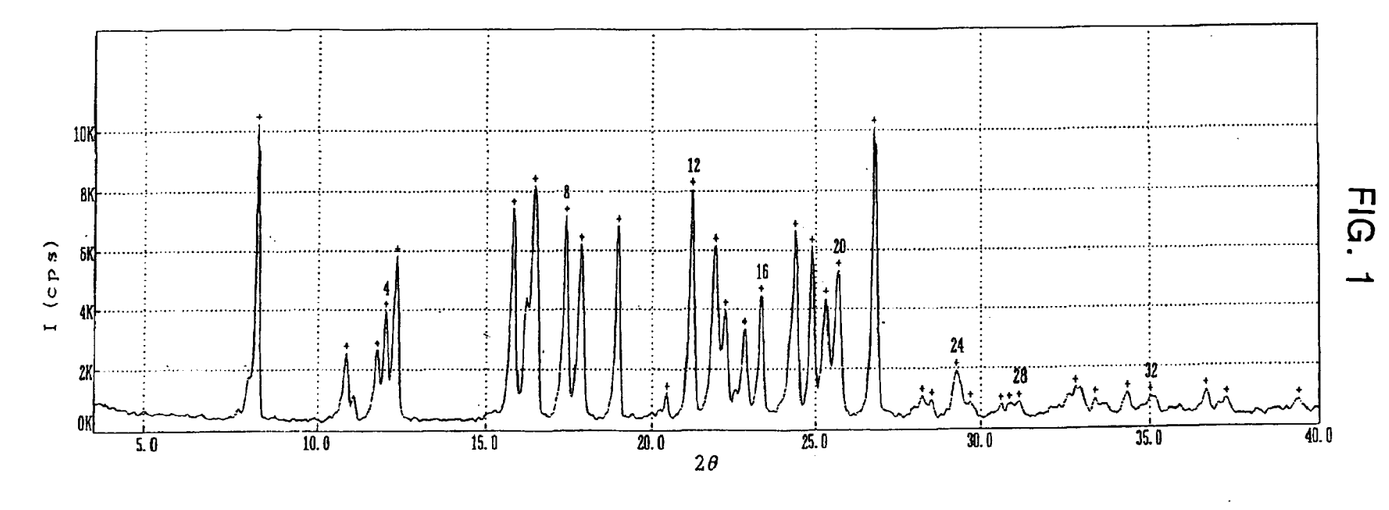
FIGS. 1 to 3: Powder X-ray diffraction spectra of the crystalline sibutramine methanesulfonate hemihydrate of formula (I) according to the present invention, anhydrous sibutramine methanesulfonate of formula (II), and sibutramine methanesulfonate monohydrate of formula (IV), respectively.
Figure 2:
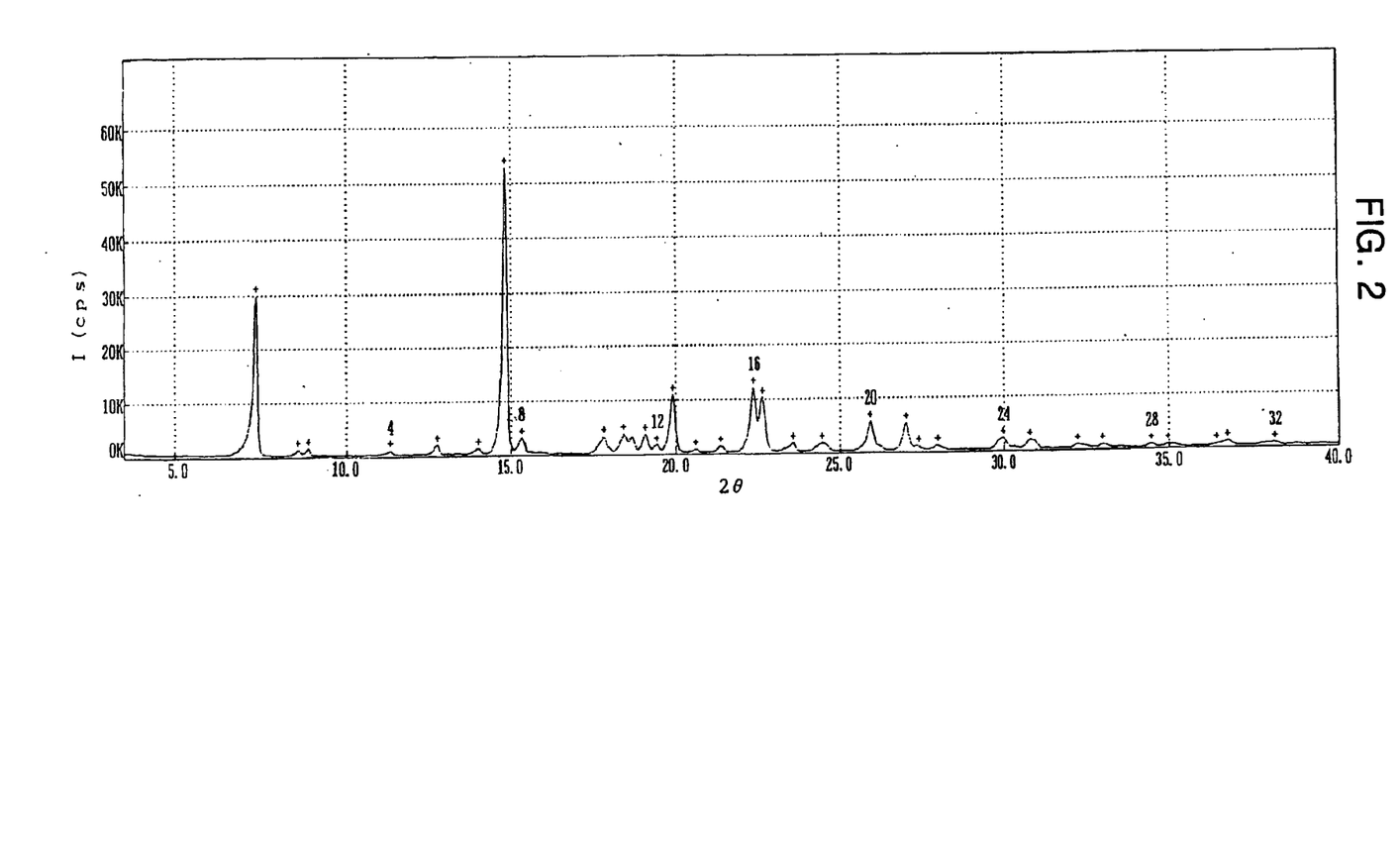
Figure 3:
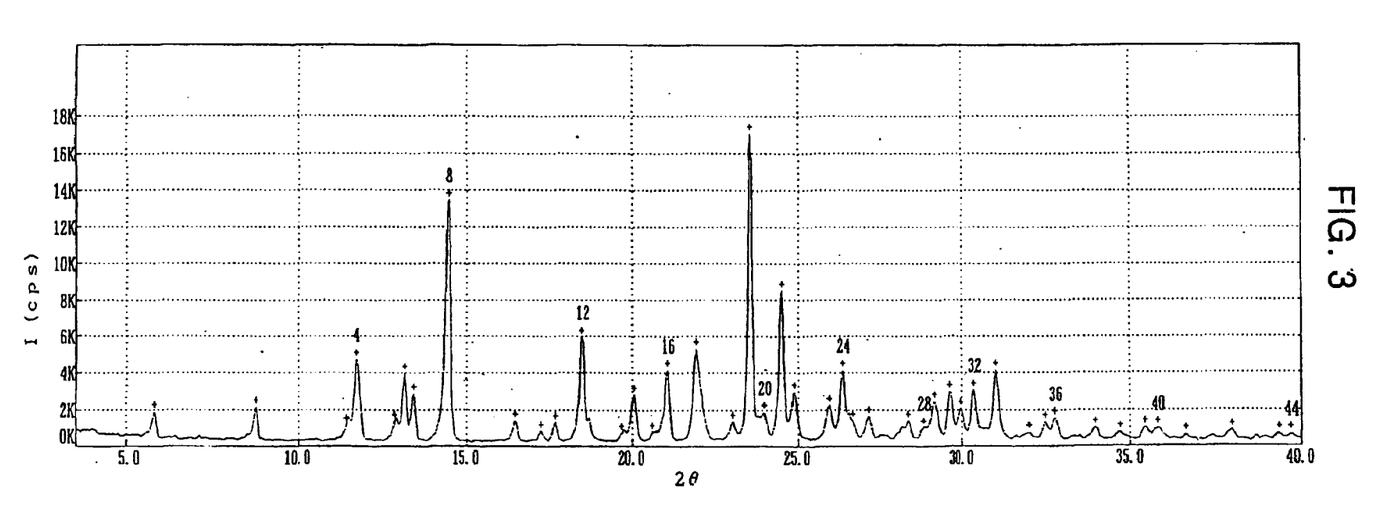
Figure 4:
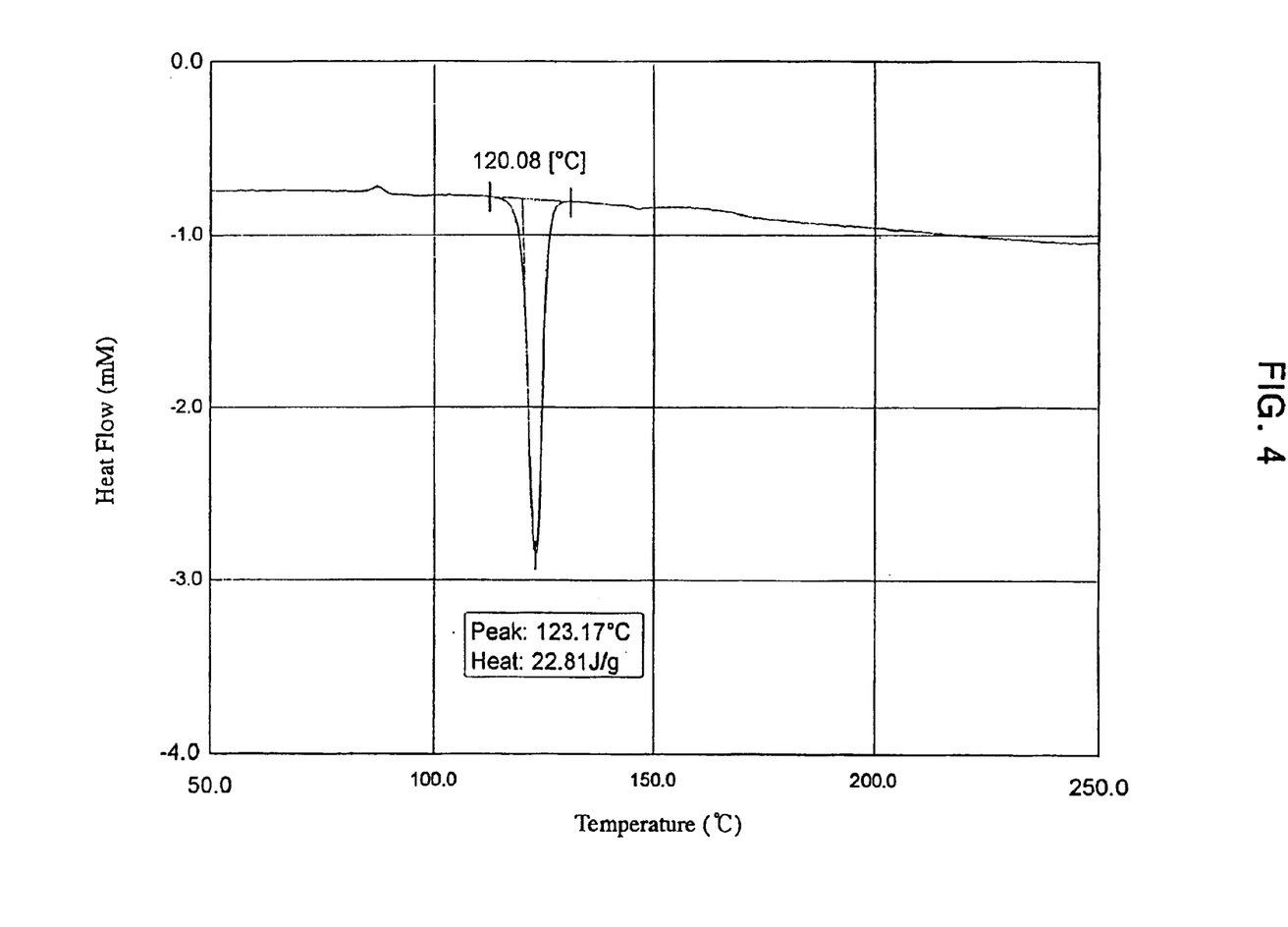
FIGS. 4 and 5: Differential scanning calorimeter thermograms of the crystalline sibutramine methanesulfonate hemihydrate of formula (I) in according to the present invention, and anhydrous sibutramine methanesulfonate of formula (II), respectively.
Figure 5:
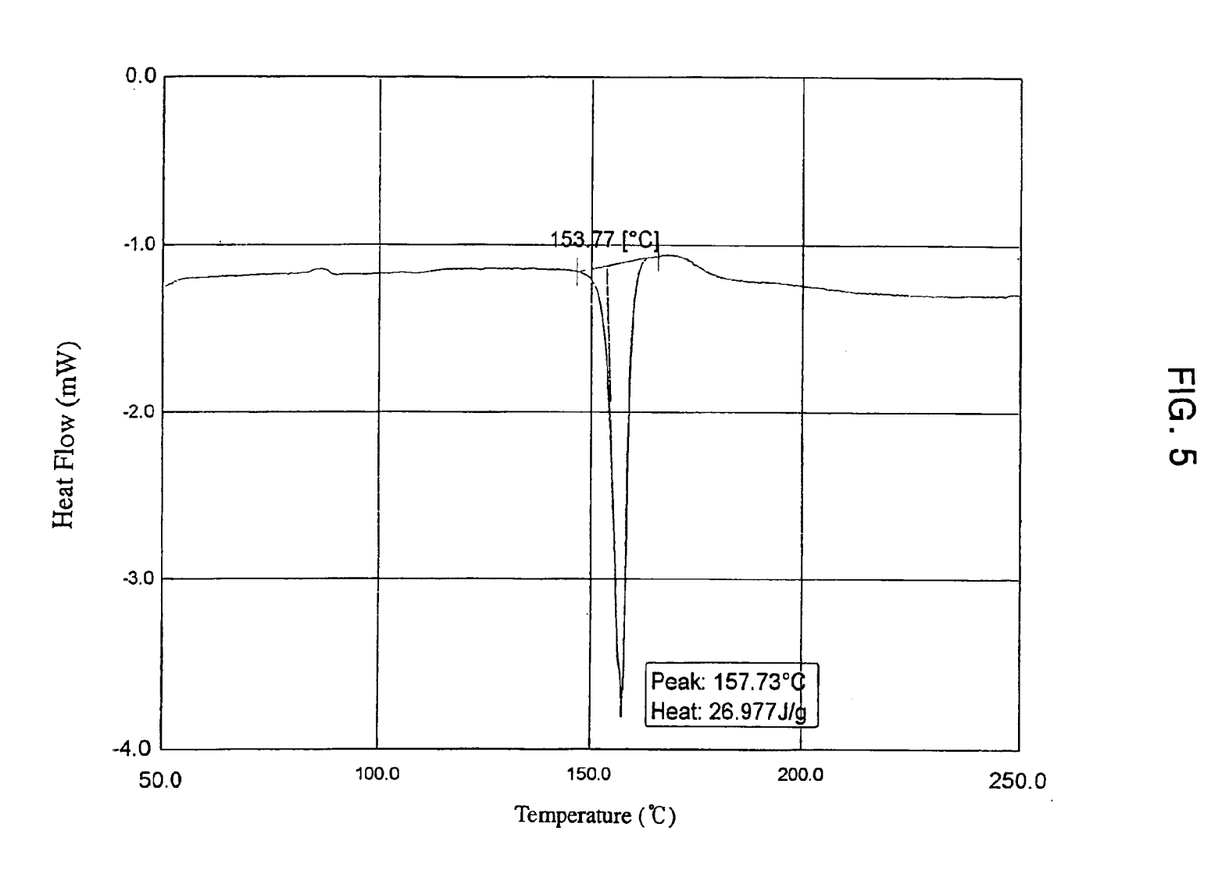

| 2θ(±0.2) | d | $I/I_o$ | 2θ | d | $I/I_o$ |
|---|---|---|---|---|---|
| 8.2 | 10.8 | 868 | 21.2 | 4.19 | 785 |
| 10.8 | 8.17 | 218 | 21.9 | 4.06 | 646 |
| 11.7 | 7.53 | 210 | 22.2 | 4.00 | 315 |
| 12.0 | 7.36 | 276 | 22.8 | 3.90 | 286 |
| 12.3 | 7.19 | 661 | 23.3 | 3.81 | 456 |
| 15.8 | 5.61 | 716 | 24.4 | 3.65 | 537 |
| 16.4 | 5.39 | 725 | 24.9 | 3.58 | 596 |
| 17.4 | 5.10 | 792 | 25.3 | 3.52 | 322 |
| 17.8 | 4.97 | 498 | 25.6 | 3.47 | 351 |
| 19.0 | 4.68 | 556 | 26.8 | 3.33 | 1000 |

EXPERIMENTAL EXAMPLE 1

Solubility in Water

Sibutramine methanesulfonate hemihydrate of formula (I) and sibutramine hydrochloride monohydrate were each dissolved to the saturation point at pH 5.2, and then subjected to high performance liquid chromatography (HPLC) to determine the dissolved amount (based on water-free of sibutramine). The results are shown in Table 2.

TABLE 2

| Compound | Solubility in water (mg/ml, pH5.2) |
|---|---|
| Sibutramine hydrochloride monohydrate of formula (VI) | 2.8 |
| Sibutramine methanesulfonate hemihydrate of formula (I) | 2,500 |

As can be seen in Table 2, sibutramine methanesulfonate hemihydrate of formula (I) had a markedly higher solubility in water than that of sibutramine hydrochloride monohydrate of formula (IV).

EXPERIMENTAL EXAMPLE 2

Stability Under a High Humidity/Temperature Condition

The thermal stability of crystalline methanesulfonate hemihydrate of formula (I) during a long term storage was compared with that of the sibutramine hydrochloride monohydrate of formula (IV). The amounts of unchanged crystalline methanesulfonate hemihydrate of formula (I) and sibutramine hydrochloride monohydrate of formula (IV) at 60° C. after 1, 2, 3 and 6 months are shown in Table 3.

TABLE 3

| Compound | Initial | Residual rate after 1 month | Residual rate after 2 months | Residual rate after 3 months | Residual rate after 6 months |
|---|---|---|---|---|---|
| Sibutramine hydrochloride monohydrate of formula (IV) | 1.000 | 1.000 | 0.999 | 0.999 | 0.992 |
| Sibutramine methanesulfonate hemihydrate of formula (I) | 1.000 | 1.001 | 0.999 | 0.999 | 1.000 |

The above result shows that crystalline sibutramine hemihydrate is as stable as sibutramine hydrochloride monohydrate.

EXPERIMENTAL EXAMPLE 3

Non-Hydroscopic Test

Crystalline sibutramine methanesulfonate hemihydrate of formula (I), sibutramine hydrochloride monohydrate (IV) and anhydrous sibutramine methanesulfonate were each exposed to a high temperature/humidity condition of 40° C. and 75% relative humidity for 1, 2, and 5 days, and the water content thereof was measured by employing Kaal-Fisher moisture analyzer. The results are shown in Table 4.

A similar series of experiments were conducted at 40° C. and 10% relative humidity, in order to examine whether the respective compounds are stable under a relatively dry condition.

TABLE 4

| Temperature (° C.) Relative humidity (° C.) | Storage time (day) | Sibutramine methanesulfonate of formula (I) | Sibutramine hydrochloride monohydrate of formula (IV) | Anhydrous sibutramine methanesulfonate of formula (II) |
|---|---|---|---|---|
| 40° C. | 1 | 2.27 | 5.40 | 0.60 |
| 75% | 2 | 2.30 | 5.45 | 2.20 |
|  | 5 | 2.30 | 5.48 | 2.25 |
| 40° C. | 1 | 2.27 | 5.40 | 0.60 |
| 10% | 2 | 2.25 | 5.36 | 0.71 |
|  | 5 | 2.26 | 5.36 | 0.70 |

As can be seen in Table 4, crystalline sibutramine methanesulfonate hemihydrate of formula (I) is non-hygroscopic under a high humidity condition, while it does not release the water of crystallization under a dry condition.

EXPERIMENTAL EXAMPLE 4

Weight Loss Effect 16 each of overweight Zuker rats (fa/fa) and thin Zuker rats (Fa/Fa) were divided into drug-administrating and control groups (8 rats per group), and the weight of each rat was measured prior to the test. A 3 mg/kg dose of crystalline sibutramine methanesulfonate hemihydrate was administrated to each rat of the drug-administrating groups, whiling the vehicle was administered to those of the control groups, everyday for 21 days. During the period, rats were allowed free access to high-fat food, and the average weights of the drug-administrating and control groups were determined in order to calculate the weight gain and loss.

TABLE 5

|  | Overweight Zuker rats | | Thin Zuker rats | |
|---|---|---|---|---|
|  | the drug-administrating group | the control group | the drug-administrating group | the control group |
| The average weigh before test (g: A) | 332.2 | 333.2 | 245.0 | 244.8 |
| The average weight after test (g: B) | 455.6 | 486.2 | 303.4 | 323.6 |
| Weight gain (g: B − A) | 123.4 | 153.0 | 58.4 | 78.8 |
| Weight loss effect (g: (Gain in weight of the control group) − (Gain in weight of the drug-administrating group)) | 29.6 | | 20.4 | |

As can be shown in Table 5, the group administrated with crystalline methanesulfonate hemihydrate of formula (I) showed a remarkable weight loss effect, as compared with the control group. Accordingly, it was demonstrated that crystalline methanesulfonate hemihydrate of formula (I) is available for treating or preventing obesity.

COMPARATIVE EXAMPLE

Attempted Preparation of (+)- and (−)-Sibutramine Methanesulfonate Hemihydrate (1) Optical Resolution of Sibutramine of Formula (II) (Preparation of (+)- and (−)-Sibutramine of Formula (II))

12.3 g of racemic sibutramine was dissolved in 85 ml of ethyl acetate, L-DBTA dissolved in 85 ml of ethyl acetate was added thereto. The reaction mixture was heated under reflux, cooled to room temperature and then filtered to obtain crystals (ee: about 85%). And then, the crystals were suspended in 220 ml of ethyl acetate, and heated under reflux to obtain solids. The solids were recrystallized from 450 ml of isopropyl alcohol to obtain L-DBTA salt of (−)-sibutramine (ee: ≧99.3%). The L-DBTA salt of (−)-sibutramine was neutralized with saturated sodium bicarbonate, and then extracted with chloroform to obtain (−)-sibutramine free base.

The filtrate obtained by filtration after reacting with L-DBTA was neutralized to pH 8.5 with sodium hydroxide, and then extracted with chloroform to obtain (+)-sibutramine, which was nearly pure (+)-isomer. D-DBTA was added thereto to obtain crystals and the crystals were recrystallized from 450 ml of isopropyl alcohol to obtain D-DBTA salt of (+)-sibutramine (ee: ≧99.3%). The D-DBTA salt of (−)-sibutramine was neutralized to pH 8.5 with saturated sodium bicarbonate, and then extracted with chloroform to obtain (+)-sibutramine free base.

(2) Preparation of (+) and (−)-Sibutramine Methanesulfonate (+)- and (−)-sibutramine free bases prepared in above (1) were treated according to the same method as that described in 2-1-2) of Example 2 to prepare the respective anhydrous methanesulfonate.

(+)-sibutramine methanesulfonate: m.p. 156.5~157.5° C., water-content 0.30%;

(−)-sibutramine methanesulfonate: m.p. 156.5~157.5° C., water-content 0.05%.

(3) Attempt to Prepare (+)- and (−)-Sibutramine Methanesulfonate Hemihydrate

Anhydrous (+)- and (−)-sibutramine methanesulfonate prepared in (2) were each treated according to the same method as that described in 2-2) of Example 2. However, no crystal formation was observed.

Accordingly, the solvent of (+)- or (−)-sibutramine methanesulfonate was replaced with toluene to induce crystal formulation. However, the crystals obtained had the same melting points/water-contents as those of anhydrous (+)- and (−)-sibutramine methanesulfonate prepared in above (2), respectively.

Further, anhydrous (+)- and (−)-sibutramine methanesulfonate were each placed for 1 day at room temperature under 75% relative humidity. Each melted within 2 hours, and became a transparent liquid in 1 day.

The above results showed that sibutramine methanesulfonate hemihydrate of formula (I) cannot be prepared from either enantiomer.

While the invention has been described with respect to the above specific embodiments, it should be recognized that various modifications and changes may be made to the invention by those skilled in the art which also fall within the scope of the invention as defined by the appended claims.

What is claimed is:

1. A pharmaceutical composition for treating or preventing obesity, comprising the crystalline sibutramine methanesulfonate hemihydrate of formula (I):

·CH$_3$SO$_3$H·1/2H$_2$O (I)

2. The pharmaceutical composition of claim 1, wherein the 2θ values of the major peaks in the X-ray diffraction spectrum of the crystalline sibutramine methanesulfonate hemihydrate are:

8.2±0.2, 10.8±0.2, 11.7±0.2, 12.0±0.2, 12.3±0.2, 15.8±0.2, 16.4±0.2, 17.4±0.2, 17.4±0.2, 17.8±0.2, 19.0±0.2, 21.2±0.2, 21.9±0.2, 22.2±0.2, 22.8±0.2, 23.3:±0.2, 24.4±0.2, 24.9±0.2, 25.3±0.2, 25.6±0.2 and 26.8±0.2.

3. The pharmaceutical composition of claim 1, further comprising a pharmaceutically acceptable carrier, diluent or excipient.

4. The pharmaceutical composition of claim 1, wherein the crystalline sibutramine methanesulfonate hemihydrate of formula (I) is present in an amount ranging from 1 to 50 mg.

5. The crystalline sibutramine methanesulfonate hemihydrate of formula (I):

·CH$_3$SO$_3$H·1/2H$_2$O (I)

6. The crystalline sibutramine methanesulfonate hemihydrate of formula (I) of claim 5, of which the 2θ values of the major peaks in the X-ray diffraction spectrum are:

8.2±0.2, 10.8±0.2, 11.7±0.2, 12.0±0.2, 12.3±0.2, 15.8±0.2, 16.4±0.2, 17.4±0.2, 17.4±0.2, 17.8±0.2, 19.0±0.2, 21.2±0.2, 21.9±0.2, 22.2±0.2, 22.8±0.2, 23.3:±0.2, 24.4±0.2, 24.9±0.2, 25.3±0.2, 25.6±0.2 and 26.8±0.2.

7. A method of preparing the crystalline sibutramine methanesulfonate hemihydrate according to claim 5, which comprises reacting sibutramine of formula (II) with methanesulfonic acid dissolved in a mixture of an organic solvent and water:

(II)

8. The method of claim 7, wherein methanesulfonic acid is employed in an amount ranging from 1 to 2 mole equivalents, based on 1 mole of sibutramine of formula (II).

9. The method of claim 7, wherein water is employed in an amount ranging from 0.5 to 5 mole equivalents, based on 1 mole of sibutramine of formula (II).

10. The method of claim 7, wherein the organic solvent is an ester selected from the group consisting of ethyl acetate, n-propyl acetate, isopropyl acetate and n-butyl acetate; an ether selected from the group consisting of diethyl ether, diisopropyl ether and t-butyl methyl ether; a ketone selected from the group consisting of acetone, methyl ethyl ketone; or a mixture thereof.

11. A method of preparing the crystalline sibutramine methanesulfonate hemihydrate according to claim 5, which comprises (i) reacting sibutramine of formula (II) with methanesulfonic acid in an anhydrous organic solvent to obtain anhydrous sibutramine methanesulfonate of formula (III); and (ii) bringing the sibutramine methanesulfonate of formula (III) into contact with water in an organic solvent:

(II)

·CH$_3$SO$_3$H (III)

12. The method of claim 11, wherein methanesulfonic acid is employed in an amount ranging from 1 to 2 mole equivalents, based on 1 mole of sibutramine of formula (II).

13. The method of claim 11, wherein water is employed in an amount ranging from 0.5 to 5 mole equivalents, based on 1 mole of anhydrous sibutramine methanesulfonate of formula (III).

14. The method of claim 11, wherein the anhydrous organic solvent of step (i) is an ester selected from the group consisting of ethyl acetate, n-propyl acetate, isopropyl acetate and n-butyl acetate; a ketone solvent selected from the group consisting of acetone, methyl ethyl ketone and methyl isobutyl ketone; an ether selected from the group consisting of ethyl ether, isopropyl ether and t-butyl methyl ether; toluene; or a mixture thereof.

15. The method of claim 11, wherein the organic solvent of step (ii) is an ester selected from the group consisting of ethyl acetate, n-propyl acetate, isopropyl acetate and n-butyl acetate; an ether selected from the group consisting of diethyl ether, diisopropyl ether and t-butyl methyl ether; a ketone selected from the group consisting of acetone, methyl ethyl ketone and methyl isobutyl ketone; or a mixture thereof.

16. The pharmaceutical composition of claim 2, further comprising a pharmaceutically acceptable carrier, diluent or excipient.

17. A method of preparing the crystalline sibutramine methanesulfonate hemihydrate according to claim 6, which comprises reacting sibutramine of formula (II) with methanesulfonic acid dissolved in a mixture of an organic solvent and water:

(II)

18. The method of claim 17, wherein methanesulfonic acid is employed in an amount ranging from 1 to 2 mole equivalents, based on 1 mole of sibutramine of formula (II).

19. The method of claim 17, wherein water is employed in an amount ranging from 0.5 to 5 mole equivalents, based on 1 mole of sibutramine of formula (II).

20. The method of claim 17, wherein the organic solvent is an ester selected from the group consisting of ethyl acetate, n-propyl acetate, isopropyl acetate and n-butyl acetate; an ether selected from the group consisting of diethyl ether, diisopropyl ether and t-butyl methyl ether; a ketone selected from the group consisting of acetone, methyl ethyl ketone; or a mixture thereof.

21. A method of preparing the crystalline sibutramine methanesulfonate hemihydrate according to claim 6, which comprises (i) reacting sibutramine of formula (II) with methanesulfonic acid in an anhydrous organic solvent to obtain anhydrous sibutramine methanesulfonate of formula (III); and (ii) bringing the sibutramine methanesulfonate of formula (III) into contact with water in an organic solvent:

(II)

(III)

22. The method of claim 21, wherein methanesulfonic acid is employed in an amount ranging from 1 to 2 mole equivalents, based on 1 mole of sibutramine of formula (II).

23. The method of claim 21, wherein water is employed in an amount ranging from 0.5 to 5 mole equivalents, based on 1 mole of anhydrous sibutramine methanesulfonate of formula (III).

24. The method of claim 21, wherein the anhydrous organic solvent of step (i) is an ester selected from the group consisting of ethyl acetate, n-propyl acetate, isopropyl acetate and n-butyl acetate; a ketone solvent selected from the group consisting of acetone, methyl ethyl ketone and methyl isobutyl ketone; an ether selected from the group consisting of ethyl ether, isopropyl ether and t-butyl methyl ether; toluene; or a mixture thereof.

25. The method of claim 21, wherein the organic solvent of step (ii) is an ester selected from the group consisting of ethyl acetate, n-propyl acetate, isopropyl acetate and n-butyl acetate; an ether selected from the group consisting of diethyl ether, diisopropyl ether and t-butyl methyl ether; a ketone selected from the group consisting of acetone, methyl ethyl ketone and methyl isobutyl ketone; or a mixture thereof.

26. A method of treating or preventing obesity in a human being or animal, by administering a therapeutically effective amount of the crystalline sibutramine methanesulfonate hemihydrate of formula (I):

(I)

27. The method of claim 26, wherein the 2θ values of the major peaks in the X-ray diffraction spectrum of the crystalline sibutramine methanesulfonate hemihydrate are:
8.2±0.2, 10.8±0.2, 11.7±0.2, 12.0±0.2, 12.3±0.2, 15.8±0.2, 16.4±0.2, 17.4±0.2, 17.4±0.2, 17.8±0.2, 19,0±0.2, 21.2±0.2, 21.9±0.2, 22.2±0.2, 22.8±0.2, 23.3±0.2, 24.4±0.2, 24,9±0.2, 25.3±0.2, 25.6±0.2 and 26.8±0.2.

28. The method of claim 26, wherein the crystalline sibutramine methanesulfonate hemihydrate is orally administered.

29. The method of claim 26, wherein the crystalline sibutramine methanesulfonate hemihydrate is administered in an amount ranging from 1 to 50 mg per day.

* * * * *